(12) United States Patent
Kiernan et al.

(10) Patent No.: US 9,783,600 B2
(45) Date of Patent: Oct. 10, 2017

(54) APOLIPOPROTEIN C3 (APOCIII) ANTAGONISTS AND METHODS OF THEIR USE TO REMOVE APOCIII INHIBITION OF LIPOPROTEIN LIPASE (LPL)

(71) Applicant: iMetabolic Biopharma, LLC, Chandler, AZ (US)

(72) Inventors: Urban A. Kiernan, Chandler, AZ (US); David A. Phillips, Peoria, AZ (US); Eric E. Niederkofler, Phoenix, AZ (US)

(73) Assignee: iMBP Holding, LLC, Chandler, AZ (US)

( * ) Notice: Subject to any disclaimer, the term of this patent is extended or adjusted under 35 U.S.C. 154(b) by 0 days.

(21) Appl. No.: 14/770,395

(22) PCT Filed: Feb. 25, 2014

(86) PCT No.: PCT/US2014/018312
§ 371 (c)(1),
(2) Date: Aug. 25, 2015

(87) PCT Pub. No.: WO2014/131008
PCT Pub. Date: Aug. 28, 2014

(65) Prior Publication Data
US 2016/0009792 A1 Jan. 14, 2016

Related U.S. Application Data

(60) Provisional application No. 61/768,931, filed on Feb. 25, 2013.

(51) Int. Cl.
*A61K 39/00* (2006.01)
*A61K 39/395* (2006.01)
*C07K 16/18* (2006.01)
*G01N 33/92* (2006.01)
*A61K 45/06* (2006.01)
*C12N 9/18* (2006.01)
*C12Q 1/44* (2006.01)

(52) U.S. Cl.
CPC .......... *C07K 16/18* (2013.01); *A61K 39/3955* (2013.01); *A61K 45/06* (2013.01); *C12N 9/18* (2013.01); *C12Q 1/44* (2013.01); *G01N 33/92* (2013.01); *A61K 2039/505* (2013.01); *C07K 2317/76* (2013.01); *C12Q 2521/537* (2013.01); *G01N 2500/00* (2013.01)

(58) Field of Classification Search
None
See application file for complete search history.

(56) References Cited

U.S. PATENT DOCUMENTS

| 2003/0165503 A1 | 9/2003 | Fruchart et al. |
| 2004/0224304 A1 | 11/2004 | Berggren |
| 2005/0287137 A1* | 12/2005 | Dhaese ................ C07K 16/18 424/141.1 |
| 2012/0328630 A1 | 12/2012 | Berggren et al. |

FOREIGN PATENT DOCUMENTS

| WO | WO 03/020765 A2 | 3/2003 |
| WO | WO 2004/081046 A2 | 9/2004 |
| WO | WO 2005/011724 A1 | 2/2005 |
| WO | WO 2012/149495 A1 | 11/2012 |

OTHER PUBLICATIONS http://web.archive.org/web/20110911141041/http://www.labome.com/gene/human/APOC3- . . . (downloaded Aug. 3, 2016).*
Johnson et al., "Dansyl phosphatidylethanolamine—labeled very low density lipoproteins. A fluorescent probe for monitoring lipolysis." *J. Biol. Chem.* 255(8), pp. 3461-3465, Apr. 25, 1980.
Samuel et al., "Lipid-induced insulin resistance: unravelling the mechanism," *The Lancet,* vol. 375, pp. 2267-2277, Jun. 26, 2010.
ISA/US Patent Office, Supplementary International Search Report and Written Opinion for Application No. PCT/US2014/018312, dated May 12, 2014 (3 pages).
Gaudet et al., "Targeting APOC3 in the Familial Chylomicromenia Syndrome," *New Engl J Med.* 371:2200-2206, 2014.
McConathy et al., "Inhibition of Lipoprotein Lipase Activity by Synthetic Peptides of Apolipopprotein C-III," *J Lipid Res.* 33:995-1003, 1992.
EP14753632.0 Supplementary EP Search Report and Written Opinion dated Oct. 21, 2016 (11 pages).

* cited by examiner

*Primary Examiner* — Shulamith H Shafer
(74) *Attorney, Agent, or Firm* — Klarquist Sparkman, LLP

(57) ABSTRACT

Provided herein are methods of increasing lipoprotein lipase (LPL) activity, by inhibiting apolipoprotein C3 (ApoCIII), which removes the ApoCIII inhibition of LPL, and permits VLDL to be converted to LDL. Also provided are methods for treating or preventing a lipid metabolism disorder, such as type 2 diabetes by use of an ApoCIII antagonist. Also provided are screening methods to identify ApoCIII antagonists.

4 Claims, 11 Drawing Sheets

APOLIPOPROTEIN C3 (APOCIII) ANTAGONISTS AND METHODS OF THEIR USE TO REMOVE APOCIII INHIBITION OF LIPOPROTEIN LIPASE (LPL)

CROSS-REFERENCE TO RELATED APPLICATION

This is the U.S. National Stage of International Application No. PCT/US2014/018312, filed Feb. 25, 2014, which was published in English under PCT Article 21(2), which in turn claim the benefit of U.S. Provisional Application No. 61/768,931, filed Feb. 25, 2013, both herein incorporated by reference.

FIELD

This application provides inhibitors of apolipoprotein C3 (ApoCIII), and methods of their use to remove the ApoCIII inhibition of lipoprotein lipase (LPL), for example to treat lipid metabolism disorders, such as hypertriglycidemia, non-alcoholic fatty liver disease, and obesity.

BACKGROUND

Very low density lipoprotein (VLDL) is a component of all human lipid profiles and increases in plasma concentration after the consumption of fatty meals. VLDL is converted to low density lipoprotein (LDL) by the enzyme lipoprotein lipase (LPL), a homodimeric enzyme that attaches the amino-glycan surface of the endothelium. The action of LPL is the liberation of free fatty acids (FFA) from the triglycerides present specifically in the VLDL particle. In the LPL mediated lipid hydrolysis, FFA are generated and subsequently transported into the adjacent cells. During this process, the VLDL reduces in physical size (due to decreased lipid content) and converted to LDL, at which time the particle is released back into the blood stream and subsequently proceeds to the liver. This transformation of the lipid particle from VLDL to LDL by LPL also results in altered apolipoprotein content of the particles. One apolipoprotein, apolipoprotein CM (ApoCIII), is a heterogeneous protein that constitutes on average 53% of the apoliprotein content of VLDL particles. The resultant LDL particle is essentially devoid of ApoCIII, as it is released free into the blood stream during the LPL digestion process.

ApoCIII is an inhibitor of LPL. Free ApoCIII is scavenged in the blood stream by other VLDL particles or the high density lipoprotein (HDL) particle as a part of the normal lipoprotein cycle. The elevation of ApoCIII concentration in plasma has been consistently correlated with the full spectrum of lipid metabolism disorders. There are rare disorders that result in overexpression of ApoCIII, which results in severe hyperlipidemia and illness of sufferers. There is also a rare null ApoCIII condition, found in Amish populations, that offers lipid protection. Even though these correlations have been observed, it has been viewed as responsive to the development of the indication, not causative.

Resent research has indicated that the presence of ectopic fat plays a major role in the organ dysfunction associated with these diseases. The development of lipid droplet and diacylglycerol (DAG) deposits in these tissues has been shown to disrupt the natural intra-cellular phospho-signalling pathways. The disruption of these pathways eventually leads to cellular and organ failure, resulting in the development of disease. However, the source of this high (DAG) content ectopic fat remains unknown.

It is proposed herein that inhibition of LPL leads to the development of these ectopic lipid accumulations developing into the spectrum of lipid metabolism disorders. Provided herein are inhibitors (antagonists) of ApoCIII, which prevent its ability to inhibit LPL, thereby preserving the LPL activity. This preservation will maintain the efficient conversion of VLDL to LDL and the generation of these ectopic lipid metabolism byproducts.

SUMMARY

The present disclosure provides methods of increasing or preserving the activity of lipoprotein lipase (LPL), for example in vitro or in vivo. In particular examples, the method includes contacting or incubating apolipoprotein C III (ApoCIII) with an effective amount of an agent that antagonizes the inhibitory action of ApoCIII, thereby increasing or preserving LPL activity.

Also provided are methods of treating or preventing a lipid metabolism disorder in a subject, such as a mammalian subject having one or more of high triglycerides (hypertriglycedemia), non-alcoholic fatty liver disease, non-alcoholic steatohepatitis, polycystic ovary syndrome, kidney disease, obesity or type 2 diabetes mellitus (insulin resistance). For example, such methods can be used to slow the progression of such lipid metabolism disorders. In particular examples, the method includes administering to the subject a therapeutically effective amount of an agent that antagonizes the inhibitory action of ApoCIII, thereby increasing or preserving the activity of LPL and treating the lipid metabolism disorder. In some examples the method further includes selecting a subject having or at risk for developing the lipid metabolism disorder that can be treated or prevented by increasing LPL activity. Exemplary agents that antagonize the inhibitory action of ApoCIII are those that bind to the C-terminus of ApoCIII, such as a monoclonal antibody (mAb) or fragment thereof that specifically binds to the C-terminus of ApoCIII (such as an Ab that binds in a region of the C-terminus (such as amino acids 41-79), for example an Ab that binds to a region containing the C-terminal 39 amino acids, C-terminal 35 amino acids, C-terminal 30 amino acids, C-terminal 25 amino acids, C-terminal 20 amino acids, C-terminal 15 amino acids, or C-terminal 10 amino acids). One specific example of such an antagonist is rabbit mAb Epitopmics catalog number 2216-1.

The disclosure also provides methods of treating or preventing a disorder that can be treated or prevented by increasing or preserving LPL activity. Such a method can include selecting a subject having or at risk for developing the disorder that can be treated or prevented by increasing LPL activity and administering to the subject one or more ApoCIII antagonists, thereby increasing or preserving LPL activity.

Also provided is an in vitro method of screening for ApoCIII antagonists. In some examples, the method includes contacting a labeled VLDL probe (such as a fluorescently-labeled VLDL probe) with LPL and one or more test agents, and then monitoring the label over time, for example monitoring the amount or intensity of the label. It is determined that the test agent is an ApoCIII antagonist when detection of a change in amount or intensity of the label over time is observed (as this indicates the presence of LPL activity). Alternatively, it is determined that the test agent is not an ApoCIII antagonist when detection of no significant change in amount or intensity of the label over time is observed (as this indicates the absence of LPL activity). Such a method can further include selecting one or more test agents determined to be an ApoCIII antagonist using the method and testing the one or more test agents determined to be an ApoCIII antagonist in vivo, for example in an animal model.

The foregoing and other objects and features of the disclosure will become more apparent from the following detailed description, which proceeds with reference to the accompanying figures.

SEQUENCE LISTING

Figure 1:
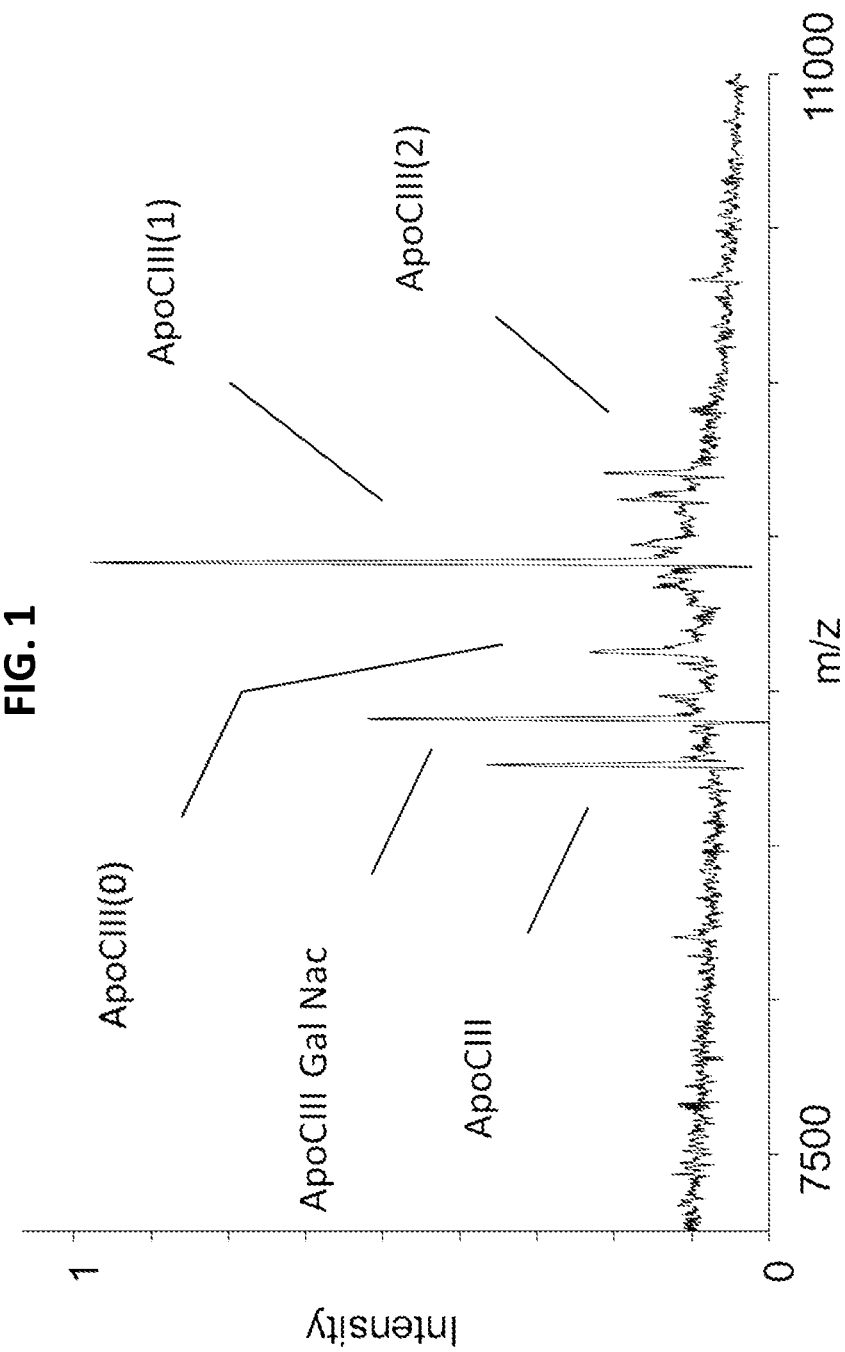
FIG. 1 is a graph showing a mass spectrometry trace and the ability of an ApoCIII mAb to detect free ApoCIII in human plasma.

The Sequence Listing is submitted as an Annex C/St.25 text file, named "sequence listing.txt," created on Aug. 24, 2015, ~784 bytes, which is incorporated by reference herein.

SEQ ID NO: 1 shows the C-terminal 39 amino acids of ApoCIII.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising an ApoCIII antagonist" includes single or plural antagonist and is considered equivalent to the phrase "comprising at least one ApoCIII antagonist." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All GenBank accession numbers and references provided herein are incorporated by reference (for GenBank, the sequence present on Feb. 25, 2013 is incorporated by reference).

Administration:

The introduction of a composition, such as an apolipoprotein C3 (ApoCIII) antagonist, into a subject by a chosen route, for example topically, orally, intravascularly (such as intravenously), intramuscularly, intraperitoneally, intranasally, intradermally, transdermally, intrathecally, subcutaneously, via inhalation or via suppository. Administration can be local or systemic, such as intravenous or intramuscular. For example, if the chosen route is intravenous, the composition is administered by introducing the composition into a vein of the subject. In some examples an ApoCIII antagonist is administered to a subject at an effective dose.

Antagonist of Apolipoprotein C3 (ApoCIII):

An agent that binds to ApoCIII protein (such as a primate or human ApoCIII) and decreases the activity of ApoCIII. For example an antagonist of human ApoCIII decreases the inhibitory function of ApoCIII, and thus increases or preserves the activity of LPL. Such antagonist can be used to treat or prevent diseases where increased/preserved LPL activity is desired, such as a lipid metabolism disorder (for example to treat or prevent high triglycerides, non-alcoholic fatty liver disease, polycystic ovary disease, or obesity).

Antibody:

A polypeptide substantially encoded by an immunoglobulin gene or immunoglobulin genes, or antigen binding fragments thereof, which specifically binds and recognizes an analyte (antigen), such as ApoCIII or an antigenic fragment of ApoCIII. Immunoglobulin genes include the kappa, lambda, alpha, gamma, delta, epsilon and mu constant region genes, as well as the myriad immunoglobulin variable region genes.

Antibodies exist, for example as intact immunoglobulins and as a number of well characterized fragments produced by digestion with various peptidases. For instance, Fabs, Fvs, and single-chain Fvs (scFvs) that specifically bind to ApoCIII (such as human or other primate ApoCIII) or fragments of ApoCIII are ApoCIII-specific binding agents. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (such as humanized murine antibodies), heteroconjugate antibodies such as bispecific antibodies). See also, *Pierce Catalog and Handbook,* 1994-1995 (Pierce Chemical Co., Rockford, Ill.); Kuby, J., *Immunology,* 3rd Ed., W.H. Freeman & Co., New York, 1997.

Antibody fragments include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. The term "antibody," as used herein, also includes antibody fragments either produced by the modification of whole antibodies or those synthesized de novo using recombinant DNA methodologies.

Typically, a naturally occurring immunoglobulin has heavy (H) chains and light (L) chains interconnected by disulfide bonds. There are two types of light chain, lambda (2) and kappa 00. There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest,* U.S. Department of Health and Human Services, 1991, hereby incorporated by reference in its entirety). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs are sometimes referred to as CDR L1, CDR L2, and CDR L3. Heavy chain CDRs are sometimes referred to as CDR H1, CDR H2, and CDR H3.

References to "$V_H$" or "VH" refer to the variable region of an immunoglobulin heavy chain, including that of an antibody fragment, such as Fv, scFv, dsFv or Fab. References to "$V_L$" or "VL" refer to the variable region of an immunoglobulin light chain, including that of an Fv, scFv, dsFv or Fab.

A "monoclonal antibody" (mAb) is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies. In some examples monoclonal antibodies are isolated from a subject. The amino acid sequences of such isolated monoclonal antibodies can be determined.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they are substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example, see U.S. Pat. No. 5,585,089).

Apolipoprotein CIII or C3 (ApoCIII): (OMIM 107720) A protein component of very low density lipoprotein (VLDL) and high density lipoprotein (HDL), which inhibits lipoprotein lipase (LPL), and plasma triglyceride catabolism. The human ApoCIII gene was mapped to chromosome 11q23.3.

ApoCIII is expressed as a 79 amino acid protein with an o-linkage glycosylation on threonine at position 74 (C-terminus). This glycosylation contains constant N-Acetylgalactosamie (GalNAc) and Galactose (Gal) residues and differ by the presence of zero, one, or two sialic acid residues in the three most abundant isoforms. Apolipoprotein CIII(1), the isoform containing a single sialic acid, has the highest inhibitory action against LPL and has the highest correlation with the presence of certain lipid metabolism disorders.

Exemplary ApoCIII sequences are publicly available, for example on GENBANK®, for example accession numbers NM_000040.1 and NG_008949.1 disclose human ApoCIII nucleic acid sequences, accession number XM_001090312.2 discloses a rhesus monkey ApoCIII nucleic acid sequence, accession number L00627.1 discloses a pig ApoCIII nucleic acid sequence, accession number XP_001090312.1 discloses a rhesus monkey ApoCIII amino acid sequence, accession number AAA30993.1 discloses a pig ApoCIII amino acid sequence, and accession numbers NP_000031.1, AAB59372.1 and AAI21082.1 disclose human ApoCIII protein sequences (wherein the mature ApoCIII sequence is the 79 amino acids following the N-terminal 20 amino acid signal peptide; i.e., amino acids 1-20=signal; amino acids 21-79=mature peptide) (as available on Feb. 25, 2013, incorporated by reference herein). It is understood that an ApoCIII sequence could have variations from what is given in GENBANK®, for example variants recognized by those skilled in the art as ApoCIII.

ApoCIII Activity:

Includes the ability to decrease or inhibit the activity of LPL.

Binding Affinity:

Affinity of an antibody or antigen binding fragment thereof for an antigen. For example, under designated conditions, an antibody that binds preferentially to ApoCIII and does not bind in a significant amount to other proteins or polysaccharides present in the sample, is referred to an antibody that specifically binds to its target. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Lipopotein Lipase (LPL) (OMIM 609708; EC 3.1.1.34)

A water soluble, calcium stabilized, homodimeric enzyme that hydrolyzes triglycerides in lipoproteins, such as those found in very low density lipoprotein (VLDL), into free fatty acids and monoacylglycerol. LPL has a high binding affinity to heparin, and is endogenously located on the surface of the endothelium through such binding to surface glycosaminoglycans. The human LPL gene was mapped to chromosome 8p21.3.

Exemplary LPL sequences are publicly available, for example on GENBANK®, for example accession numbers NM_000237.2 and BC011353.1 disclose human LPL nucleic acid sequences, accession number XM_003256730.2 discloses a northern white-cheeked gibbon LPL nucleic acid sequence, accession number NM_214286.1 discloses a pig LPL nucleic acid sequence, accession number EHH28317.1 discloses a rhesus monkey LPL amino acid sequence, accession number AAT95419.1 discloses a pig LPL amino acid sequence, and accession numbers NP_000228.1, P06858.1 and AAB59536.1 disclose human LPL protein sequences (as available on Feb. 25, 2013, incorporated by reference herein). It is understood that a LPL sequence could have variations from what is given in GENBANK®, for example variants recognized by those skilled in the art as LPL.

Pharmaceutically Acceptable Carriers:

The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of an ApoCIII antagonist.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing a Disease:

Administration of a therapeutic to a subject who does not exhibit signs of a disease or exhibits only early signs of the disease, for the purpose of decreasing the risk of developing pathology or slowing the progression of a disease. For example, a subject who is at risk to develop in the future a disease that can benefit from increased LPL activity, can be administered an ApoCIII antagonist. The preventative effect can be evidenced, for example, by a delayed onset of clinical symptoms of the disease in a susceptible subject, a reduction in severity of some or all clinical symptoms of the disease once it develops, a slower progression of the disease, an improvement in the overall health or well-being of the subject, or by other parameters well known in the art that are specific to the particular disease. Prevention of a disease does not require a total absence of disease. For example, a decrease of at least 20% or at least 50% of the symptoms can be sufficient.

Subject:

As used herein refers to living mammals, such as those that have or are at risk for developing, a lipid metabolism disorder. In particular examples, the subject is a human or non-human primate, or a veterinary subject (such as a mouse, rat, dog, cat, horse, cow, or pig).

Therapeutically Effective Amount (or Effective Amount):

A quantity of a substance, such as an ApoCIII antagonist, sufficient to restore or increase LPL activity. A therapeutic agent, such as an ApoCIII antagonist, is administered in therapeutically effective amounts. For instance, this can be the amount necessary to treat or prevent a disease that can benefit from increased LPL activity. In some embodiments, a therapeutically effective amount is the amount of one or more ApoCIII antagonists necessary to increase LPL activity or reduce a sign or symptom of a disease that can benefit from increased LPL activity (such as an increase of at least 20%, at least 50%, at least 60%, at least 75%, at least 80%, at least 95%, at least 100%, at least 200%, at least 300%, or at least 500% as compared to an absence of the one or more ApoCIII antagonists). When administered to a subject, a dosage will generally be used that will achieve target tissue concentrations that has been shown to achieve a desired in vitro effect.

Effective amounts a therapeutic agent can be determined in many different ways, such as assaying for an increase in LPL activity, for example by assaying in vitro using a VLDL probe as described in Example 2 (e.g., observing a decrease in fluorescence indicates the presence of LPL activity) and/or improvement of physiological condition of a subject having or at risk for a disease that can benefit from increased LPL activity (such as observing a decrease in blood glucose, blood triglyceride, or blood liver enzyme levels). Effective amounts also can be determined through various in vitro, in vivo or in situ assays.

Therapeutic agents can be administered in a single dose, or in several doses, for example daily, during a course of treatment. However, the effective amount of can be dependent on the agent applied, the subject being treated, the severity and type of the condition being treated, and the manner of administration.

Treating a disease: Inhibiting the full development of a disease or condition, for example, in a subject who has a disease that can benefit from increased LPL activity. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a reduction in severity of some or all clinical symptoms of the disease, a slower progression of the disease, an improvement in the overall health or well-being of the subject, or by other parameters well known in the art that are specific to the particular disease. Treatment of a disease does not require a total absence of disease. For example, a decrease of at least 20% or at least 50% of the signs or symptoms can be sufficient.

Under conditions sufficient for: A phrase that is used to describe any environment that permits the desired activity. In one example, "under conditions sufficient for" includes administering an ApoCIII antagonist to a subject sufficient to allow the antagonist to bind to ApoCIII and remove its inhibition of LPL, thereby increasing LPL activity. The conditions employed in the methods are "physiological conditions" which include reference to conditions (e.g., temperature, osmolarity, pH) that are typical inside a living primate or primate cell (or other veterinary subject). While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Overview

The present disclosure provides a novel therapeutic approach to the treatment of lipid metabolism disorders, such as high triglycerides, non-alcoholic fatty liver disease, obesity, and the like. The method preserves the function of a specific lipid metabolizing enzyme, lipoprotein lipase (LPL), by retarding the inhibitory action of ApoCIII, its molecular inhibitor. The pathogenically associated region of the ApoCIII target (the C-terminus, such as amino acids 41-79) is disclosed herein, and it is shown herein that endogenous LPL enzymatic function can be preserved through the use of an antibody (such as a mAb or mAb fragment) that binds this functional area of the ApoCIII molecule. A specific example of an antibody that binds to the C-terminus of ApoCIII is anti-ApoCIII mAb from Epitomics (Burlingame, Calif., cat#2216-1).

Thus provided herein are methods of increasing or preserving the activity of lipoprotein lipase (LPL). Such methods can include contacting or incubating ApoCIII with an effective amount of an agent that antagonizes the inhibitory action of ApoCIII, thereby increasing or preserving LPL activity. Such methods can be performed in vitro or in vivo. For example, the disclosure provides methods of treating or preventing a lipid metabolism disorder in a subject. Such methods can include administering to the subject (e.g., iv, im, ip, sc, and others known in the art) a therapeutically effective amount of an agent that antagonizes the inhibitory action of ApoCIII, thereby increasing or preserving the activity of LPL and treating the lipid metabolism disorder. Exemplary lipid metabolism disorders include but are not limited to: high triglycerides (hypertriglycedemia), non-alcoholic fatty liver disease, non-alcoholic steatohepatitis, polycystic ovary syndrome, kidney disease, obesity or type 2 diabetes mellitus (insulin resistance). In some examples, the subject has or is at risk to develop a lipid metabolism disorder that can be treated or prevented by increased LPL activity. Thus, the method can further include selecting a subject having or at risk for developing the lipid metabolism disorder that can be treated or prevented by increasing or preserving LPL activity. In some examples, the method also includes monitoring the lipid metabolism disorder subsequent to administering the agent that antagonizes the inhibitory action of ApoCIII, establishing a baseline of LPL activity in the subject prior to and/or subsequent to, administering the agent that antagonizes the inhibitory action of ApoCIII, or combinations thereof. In some examples, the subject has a blood triglyceride level of at least 200 mg/dL, a fasting plasma glucose ≥7 mmol/l, a plasma glucose ≥11.1 mmol/l (200 mg/dl) following a glucose tolerance test, a blood albumin level of at 6 g/dL, a blood alanine transaminase (ALT) level of at least 70 IU/L, a blood aspartate transaminase (AST) level of at least 50 IU/L, a blood alkaline phosphatase (ALP) level of at least 150 IU/L, a blood total bilirubin level of at least 2 mg/dL, or combinations thereof. In some examples, the method also includes administering a statin, insulin, niacin, metformin or combinations thereof at therapeutically effective amounts to the subject.

Exemplary agents that antagonize the inhibitory action of ApoCIII include agents that specifically bind to the C-terminus of ApoCIII, such as bind to a region that includes amino acids 41-79 of mature ApoCIII. In one example, the agent that antagonizes the inhibitory action of ApoCIII is a monoclonal antibody (mAb) or fragment thereof, such as anti-ApoCIII mAb from Epitomics (Burlingame, Calif., cat#2216-1). In one example, the agent that antagonizes the inhibitory action of ApoCIII is administered at a dose of at least 1 mg.

Also provided are methods of treating or preventing a disorder that can be treated or prevented by increasing or preserving LPL activity. For example, such methods can include selecting a subject having or at risk for developing the disorder that can be treated or prevented by increasing or preserving LPL activity, and administering to the subject one or more ApoCIII antagonists, thereby increasing or preserving LPL activity.

The disclosure provides in vitro screening methods for identifying ApoCIII antagonists. Such methods can include contacting a labeled VLDL probe (such as a fluorescently-labeled VLDL probe) with LPL (such as a plasma sample) and one or more test agents, and monitoring the label over time (such as a period of at least 5 minutes, at least 10 minutes, at least 30 minutes, or at least 60 minutes). A determination is made that the test agent is an ApoCIII antagonist when detection of a change in amount or intensity of the label over time is observed (as this indicates LPL activity is increasing). In contrast, it is determined that the test agent is not an ApoCIII antagonist when detection of no significant change in amount or intensity of the label over time is observed (as this indicates LPL activity is decreasing or absent). The method can further include selecting one or more test agents determined to be an ApoCIII antagonist and testing such agents for their ApoCIII antagonizing activity in vivo.

Methods of Increasing LPL Activity to Treat a Lipid Metabolism Disorder

It is shown herein that inhibiting or antagonizing ApoCIII can be effective in removing ApoCIII inhibition of LPL, thereby increasing or preserving LPL activity. Based on these results, it is proposed herein that such ApoCIII inhibitors can be used to treat disorders that will benefit from increased or preserved LPL activity, such as a lipid metabolism disorder. Lipid metabolism disorders are characterized by abnormal anabolism or catabolism of lipids. Lipid disorders tend to cluster in patients and result in the parallel or sequential development of associated indications. This abnormal lipid processing results in the development of ectopic fat of the disease afflicted tissues, which ultimately results in specific tissue-related symptoms. Examples of such disorders include, but are not limited to, hyper triglycidemia (high triglycerides), non-alcoholic fatty liver disease, type 2 diabetes mellitus (insulin resistance), obesity, non-alcoholic steatohepatitis, diabetic and chronic kidney disease, and polycystic ovary syndrome.

Based on these discoveries, it is proposed the ApoCIII-mediated shut-off of LPL-function is responsible for the decreased ability of VLDL to be converted to LDL, and development of lipid metabolism disorders, and methods are provided to increase LPL activity, for example to treat lipid metabolism disorders. Therefore, decreasing or inhibiting ApoCIII will remove its inhibition or LPL, thereby increasing or preserving LPL activity, and allowing the efficient conversion of VLDL to LDL.

Methods for increasing or preserving LPL activity are provided. In one example the method includes contacting a cell (e.g., a primate or human cell, such as an endothelial cell) or a tissue (such as blood), or a lipid particle, such as VLDL, with a therapeutically effective amount of an agent that decreases the activity of ApoCIII. In one example, the cell is an endothelial cell, such as a human endothelial cell. In one example, the therapeutically effective amount of an agent that decreases the activity of ApoCIII is contacted with secreted LPL, such as that found on an endothelial cell all or in the blood. For example, if the secreted LPL (such as that in the blood) is present in a subject, the contacting can include administering the agent that decreases the activity of ApoCIII to the subject at a therapeutically effective amount. In some examples, the ApoCIII antagonist is an antibody or functional fragment thereof, such as a monoclonal antibody that binds to human ApoCIII, for example with high specificity, as well as small molecules, such as short peptides, phospholipids (e.g., phosphatidylserine, lipids, lipoproteins, glucolipids), aptamers, or small chemical compounds.

In one example, one or more ApoCIII antagonists are used to increase or preserve LPL function or activity. Such methods can be used to treat or prevent a disorder that can benefit from increased LPL function. Examples of such disorders include high triglycerides, non-alcoholic fatty liver disease, and type 2 diabetes mellitus. In some examples, the method includes selecting a subject having or that is at risk to develop a disorder that can benefit from increased LPL activity, such as a subject having high triglycerides (e.g., a subject with a blood triglyceride level of 200 mg/dL or above), non-alcoholic fatty liver disease (e.g., a subject with both negative liver screen and ultrasound results), type 2 diabetes mellitus (e.g., a subject with a fasting plasma glucose ≥7 mmol/l (126 mg/dl) or with a glucose tolerance test, two hours after the oral dose a plasma glucose ≥11.1 mmol/l (200 mg/dl)). In a specific example, the method is a method of treating or preventing a disorder that can be treated or prevented by increasing LPL activity, and the method selecting a subject (e.g., a primate or human subject) having or at risk for developing the disorder that can be treated or prevented by increasing LPL activity and administering to the subject one or more ApoCIII antagonists, thereby increasing LPL activity.

ApoCIII Antagonists

An ApoCIII antagonist is an agent that binds (for example with high affinity) to an ApoCIII protein (such as a human or other primate ApoCIII) and decreases its inhibitory activity on LPL. For example an antagonist of ApoCIII decreases the inhibitory function of ApoCIII, and thus removes its inhibition of LPL and increases or preserves the activity of LPL. Such antagonists can be used to treat or prevent diseases where increased LPL activity is desired, such as high triglycerides, non-alcoholic fatty liver disease, and type 2 diabetes mellitus.

In one example, the ApoCIII antagonist is an antibody, such as a monoclonal or polyclonal antibody or a functional fragment thereof, which binds with high specificity to ApoCIII. In one example, the ApoCIII antagonist is a humanized antibody. In one example, the antagonist antibody binds to the C-terminal region of mature ApoCIII (amino acids 41 to 79 of mature ApoCIII make up the C-terminal region). Methods of making antibodies are routine in the art. For example, antibodies can be generated to the C-terminal 39 amino acids of ApoCIII (gwvtdgfssl kdywstvkdk fsefwdldpe vrptsavaa; SEQ ID NO: 1). For example, ApoCIII antagonist antibodies can be generated that specifically bind to an epitope within SEQ ID NO: 1, such as one that includes at least 6, at least 7, at least 8 or at least 9 contiguous amino acids of SEQ ID NO: 1. In one example, an ApoCIII antagonist antibody binds to a region that includes the C-terminal 39, C-terminal 35, C-terminal 30, C-terminal 25, C-terminal 20, C-terminal 15, C-terminal 10, or C-terminal 5 amino acids. In addition, ApoCIII antibodies that bind to ApoCIII are commercially available, for example from Epitopmics (Catalog #2216-1; Burlingame, Calif.,) Academy Biomedical (Catalog #33A-G2), and Abcam (Catalog # ab4290; Cambridge, Mass.). One can determine if such antibodies function as an ApoCIII antagonist using the methods provided herein (e.g., see Example 2).

In other examples, the ApoCIII antagonist is a peptide (such as a protein no more than about 100 amino acids, such as 5-10, 5-50, 10 to 25, or 5-100 amino acids), a lipid such as a phospholipid (e.g., phosphatidylserine), glucolipid, or lipoprotein, or a small molecule.

Based on the discoveries presented herein, ApoCIII antagonists can be identified, for example using the methods provided herein. In one example, the assays are performed in vitro, for example one or more test agents can be contacted with a VLDL probe (see Examples 1 and 2). In another example, the assays are performed in vivo, for example one or more test agents can be administered to a non-human mammal, such as a primate, or to a rodent (such as mouse) expressing ApoCIII (and in some examples having a lipid metabolism disorder).

In one example, one or more test agents, such as ApoCIII antibodies or other small molecules (such as an aptamer), can be incubated with a VLDL probe in vitro to determine their effect on LPL activity (such as an effect on observed fluorescence or other detectable signal). Such an effect can be compared to a control, such as a negative or positive control (such as vehicle only, or a known ApoCIII antagonist). For example, to measure the ability of a test agent to suppress ApoCIII suppression of LPL, an assay can be performed that measures LPL activity directly or indirectly, for example by monitoring the conversion of VLDL to LDL. Such assays are provided herein. For example, a fluorescently labeled VLDL probe (such as one from Kaleen Biomedical, LLC, Montgomery Village, Md.) can be incubated with LPL (for example using post-heparinized heparin plasma), and with one or more test agents for a period of time (such as at least 5 minutes, at least 10 minutes, at least 20 minutes, at least 30 minutes, at least 1 hour, at least 2 hours, or at least 24 hours) and fluorescence monitored over time. Parallel samples can include the same components, without the test agent, as a control. The LPL activity is determined by measuring fluorescence over time. If the test agent is an ApoCIII antagonist, the fluorescence will decrease over time, indicating conversion of VLDL to LDL. In contrast, if the test agent is not an ApoCIII antagonist, the fluorescence will not decrease over time (e.g., will remain essentially the same), indicating ApoCIII is inhibiting LPL, and preventing the conversion of VLDL to LDL.

Administration of ApoCIII Antagonists

In one example, LPL activity is increased or preserved in vivo by administering to the subject one or more ApoCIII antagonists, such as a pharmaceutical composition containing such antagonists. Although the disclosure primarily discusses in vivo uses, one skilled in the art will appreciate that the one or more ApoCIII antagonists can be used in vitro as well. Compositions that include one or more ApoCIII antagonists, such as antibodies specific for the C-terminus of ApoCIII, which can be used to increase or retain LPL activity are suited for the preparation of pharmaceutical compositions that can be used in vivo or in vitro.

Pharmaceutical compositions that include one or more ApoCIII antagonists are provided. These pharmaceutical compositions can be used in in vivo or in vitro methods of treatment/prevention of disorders that can benefit from increased LPL activity, and can be formulated with an appropriate physiologically acceptable solid or liquid carrier, depending upon the particular mode of administration chosen. A variety of aqueous carriers can be used, for example, buffered saline and the like. These solutions are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of ApoCIII antagonists in these formulations can vary widely, and will be selected primarily based on fluid volumes, viscosities, body weight and the like in accordance with the particular mode of administration selected and the subject's needs. Compositions including one or more ApoCIII antagonists are of use, for example, for the treatment of lipid metabolism disorders.

The pharmaceutically acceptable carriers and excipients useful in this disclosure, for either therapeutic or diagnostic methods, are conventional. The one or more ApoCIII antagonists can be formulated for systemic or local (such as inhalational) administration. In one example, the one or more ApoCIII antagonists are formulated for parenteral administration, such as intravenous, subcutaneous, or intramuscular administration. For instance, parenteral formulations usually include injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

The compositions can be prepared in unit dosage forms for administration to a subject. The dosage form of the pharmaceutical composition will be determined by the mode of administration chosen. For instance, in addition to injectable fluids, topical, inhalation, oral and suppository formulations can be employed. Topical preparations can include ointments, sprays and the like. Inhalation preparations can be liquid (such as solutions or suspensions) and include mists, sprays and the like. Oral formulations can be liquid (for example, syrups, solutions or suspensions), or solid (such as powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that include one or more ApoCIII antagonists can be formulated in unit dosage form suitable for individual administration. In addition, the pharmaceutical compositions may be administered in a single dose or as in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of ApoCIII antagonists over a period of a few days to months, or even years. Thus, the dosage regime will also, at least in part, be determined based on the particular needs of the subject to be treated, the severity of the affliction, whether the therapeutic agent is administered for preventive or therapeutic purposes, previous prophylaxis and therapy, the subject's clinical history and response to the therapeutic agent, and the manner of administration, and can be left to the judgment of the prescribing clinician. Within these bounds, the formulation to be administered will contain a quantity of the ApoCIII antagonists in amounts effective to achieve the desired effect in the subject being treated. A therapeutically effective amount of one or more ApoCIII antagonists is one that which provides either subjective relief of a symptom(s) or an objectively identifiable improvement as noted by the clinician or other qualified observer.

These compositions containing ApoCIII antagonists can be administered in conjunction with another agent, such as one that is used to treat high triglycerides or type 2 diabetes mellitus. For example ApoCIII antagonists can be administered in conjunction with agents for treating high triglycerides (e.g., one or more of niacin, omega-3 fatty acids, a statin, a fibrate drug (a class of amphipathic carboxylic acids, for example bezafibrate, ciprofibrate, gemifibrozil, or fenofibrate), agents for treating non-alcoholic fatty liver disease (such as insulin sensitizers (e.g., metformin and thiazolidinediones), vitamin E, or statins), agents for treating type 2 diabetes mellitus (such as metformin, sulfonylureas, nonsulfonylurea secretagogues, alpha glucosidase inhibitors, thiazolidinediones, glucagon-like peptide-1 analog, and dipeptidyl peptidase-4 inhibitors, or insulin), or combinations thereof, either simultaneously or sequentially with the ApoCIII antagonist. The one or more ApoCIII antagonists also can be used or administered as a mixture, for example in equal amounts, or individually, provided in sequence, or administered all at once.

Single or multiple administrations of the compositions can be administered depending on the dosage and frequency as required and tolerated by the subject. The composition should provide a sufficient quantity of one or more agents that increase LPL activity to effectively treat the subject or inhibit the development of the target disease. The dosage can be administered once but can be applied periodically until either a therapeutic result is achieved or until side effects warrant discontinuation of therapy. In one example, a dose of the one or more ApoCIII antagonists is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of a disease without producing unacceptable toxicity to the patient.

In one specific, non-limiting example, a unit dosage for intravenous, subcutaneous, or intramuscular administration of one or more ApoCIII antagonists includes at least 0.5 µg ApoCIII antagonist per dose, such as at least 5 µg ApoCIII antagonist per dose, at least 50 µg ApoCIII antagonist per dose, at least 500 µg ApoCIII antagonist per dose, at least 1 mg ApoCIII antagonist per dose, at least 5 mg ApoCIII antagonist per dose, or at least 10 mg ApoCIII antagonist per dose. In a specific example, the dose is about 5 mg ApoCIII antagonist. In some examples, doses are administered three-times in one week.

In one specific, non-limiting example, an ApoCIII antagonist daily dosage is from about 0.01 milligram to about 500 milligram per kilogram of animal body weight, for example given as a single daily dose or in divided doses two to four times a day, or in sustained release form. For most large mammals, the total daily dosage is from about 0.01 milligrams to about 100 milligrams per kilogram of body weight, such as from about 0.5 milligram to about 100 milligrams per kilogram of body weight, which can be administered in divided doses 1 to 4 times a day in unit dosage form containing for example from about 1 to about 50 mg (such as 5 mg) of the compound in sustained release form. In one example, the daily oral dosage in humans is between 1 mg and 1 g, such as between 1 mg and 100 mg, 10 mg and 200 mg, such as 5 mg. The dosage regimen may be adjusted within this range or even outside of this range to provide the optimal therapeutic response. Oral administration of an ApoCIII antagonist can be carried out using tablets or capsules, such as about 1 mg to about 500 mg of the agonist or antagonist. Exemplary doses in tablets include 0.1 mg, 0.2 mg, 0.25 mg, 0.5 mg, 1 mg, 2 mg, 5 mg, 10 mg, 25 mg, 50 mg, 100 mg, 250 mg, and 500 mg of the ApoCIII antagonist. Other oral forms can also have the same dosages (e.g., capsules). In one example, a dose of an ApoCIII antagonist administered parenterally is at least 1 mg, such as 1 to 500 mg, 5 to 100 mg, or 10 to 200 mg of the ApoCIII antagonist.

In one specific, non-limiting example, a unit dosage for oral administration (such as a table or capsule), or for oral intravenous or intramuscular administration, of a ApoCIII antagonist that is a protein includes about 1 µg to 1000 mg of protein per dose, such as 1 µg to 100 µg protein per dose, 1 µg to 500 µg protein per dose, 1 µg to 1 mg protein per dose, 1 mg to 1000 mg protein per dose, 1 mg to 10 mg per dose (such as 5 mg per dose), or 10 mg to 100 mg protein per dose. In some examples, doses are administered at least three-times in one week.

In one specific, non-limiting example, a unit dosage for oral administration (such as a table or capsule), or for oral intravenous or intramuscular administration, of an ApoCIII antibody includes about 1 µg to 1000 mg of antibody per dose, such as 1 µg to 100 µg antibody per dose, 1 µg to 500 µg antibody per dose, 1 µg to 10 mg protein per dose, 1 mg to 1000 mg antibody per dose, or 5 mg to 100 mg antibody per dose. In some examples, doses are administered at least three-times in one week.

Actual methods for preparing administrable compositions will be known or apparent to those skilled in the art and are described in more detail in such publications as *Remington's Pharmaceutical Science,* 19th ed., Mack Publishing Company, Easton, Pa. (1995).

ApoCIII antagonists can be provided in lyophilized form and rehydrated with sterile water before administration, although they are also provided in sterile solutions of known concentration. The resulting solution can then added to an infusion bag containing 0.9% sodium chloride, USP, and can be administered in some examples at a dosage of from 0.05 to 300 mg/kg of body weight (e.g., 0.05 to 100 mg/kg, 0.05 to 1 mg/kg, 5 to 50 mg/kg, or 10 to 40 mg/kg of body weight). Considerable experience is available in the art in the administration of antibodies, proteins or other small molecules. Such molecules can be administered by slow infusion, rather than in an intravenous push or bolus. In one example, a higher loading dose is administered, with subsequent, maintenance doses being administered at a lower level. For example, if the ApoCIII antagonist is an antibody, an initial loading dose of 5 mg may be infused over a period of some 90 minutes, followed by weekly maintenance doses for 4-8 weeks of 2 mg infused over a 30 minute period if the previous dose was well tolerated. In some examples the Abs are administered at least once a week, at least once a month, at least twice a month, or at least once every two months. In one example, at least 1 mg mAb/kg (such as at least 5 mg/kg, at least 10 mg/kg, at least 20 mg/kg or at least 40 mg/kg, such as 1 to 100 mg/kg, 1 to 50 mg/kg, 5 to 50 mg/kg, or 10-40 mg/kg) is administered to the patient every two to four weeks. In some examples, the mAbs are administered iv, subcutaneously or im.

The ApoCIII antagonist can be administered to humans or other subject using routine modes of administration, such as topically, intravascularly such as intravenously, intramuscularly, intraperitoneally, intranasally, intradermally, intrathecally, subcutaneously, intracraneally, orally, via inhalation or via suppository. The particular mode of administration and the dosage regimen will be selected by the attending clinician, taking into account the particulars of the case (for example the subject, the disease, the disease state involved, and whether the treatment is prophylactic).

Controlled release parenteral formulations of ApoCIII antagonists can be made as implants, oily injections, or as particulate systems. For a broad overview of protein delivery systems see Banga, A. J., *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, J., *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, R., *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec et al., *J. Parent. Sci. Tech.* 44:58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri, et al., *Liposome Drug Delivery Systems*, Technomic Publishing Co., Inc., Lancaster, Pa., 1993). Numerous additional systems for controlled delivery of therapeutic proteins are known (see, for example, U.S. Pat. Nos. 5,055,303; 5,188,837, 4,235,871, 4,501,728, 4,837,028 4,957,735, 5,019,369, 5,055,303; 5,514,670; 5,413,797; 5,268,164; 5,004,697; 4,902,505; 5,506,206, 5,271,961; 5,254,342 and 5,534,496).

In some embodiments, sustained release of the pharmaceutical preparation that includes a therapeutically effective amount of the one or more agents that decrease ApoCIII activity may be beneficial.

The present disclosure also includes combinations of one or more ApoCIII antagonists with one or more other agents useful in the treatment of a disorder that can benefit from increased LPL activity. For example, the compounds of this disclosure can be administered in combination with effective doses of other therapeutic agents, such as those listed above. The term "administration in combination" or "co-administration" refers to both concurrent and sequential administration of the active agents.

Subjects

Exemplary subjects that can benefit from the disclosed therapies include mammals, such as human and other primates, such as macaques, apes, and the like, as well as veterinary subjects. In one example, the subject treated has, or is at risk for developing, a disease that can benefit from increased LPL activity. In some examples, the method includes selecting a subject, such as a human, that has, or is at risk for developing, a disease that can benefit from increased LPL activity (such as any disease listed herein). In some examples, the method includes obtaining a blood sample and obtaining the subject's triglyceride value, liver enzyme values, percent liver fat content, glucose value, or combinations thereof, for example to establish such values prior to treatment or to establish that the subject will benefit from the therapies provided herein, as well as to determine if the ApoCIII antagonist is working effectively in the subject.

In one example, the subject has or is at risk to develop a disease that can be treated or prevented by increased LPL activity, such as a lipid metabolism disorder (e.g., high triglycerides, non-alcoholic fatty liver disease, obesity, polycystic ovary syndrome, non-alcoholic steatohepatitis, or type 2 diabetes mellitus (insulin resistance)). In one example the subject is obese.

In one example, the subject has or is at risk to develop high triglycerides (known as hypertriglyceridemia), which can be treated or prevented by administration of an ApoCIII antagonist to increase LPL activity. Subjects with high triglycerides show elevated levels of triglycerides, for example in their blood. In one example, high triglycerides in the blood is a value of 200 mg/dL or above, such as at least 200 mg/dL, at least 300 mg/dL, at least 400 mg/dL, or at least 500 mg/dL. Thus the disclosed methods can reduce triglyceride levels in the blood, for example by at least 10%, at least 20%, at least 30%, at least 40%, at least 50%, at least 75%, or at least 80%, for example as compared to the absence of the ApoCIII antagonist. In some cases, high triglycerides can predispose the subject to cardiovascular disease. In some examples, the subject to be treated has a blood triglyceride level of at least 200 mg/dL, at least 300 mg/dL, at least 400 mg/dL, or at least 500 mg/dL. In some examples, the methods further include determining the blood triglyceride level of the subject, for example before and/or after administration of the ApoCIII antagonist.

In one example, the subject has or is at risk to develop non-alcoholic fatty liver disease (NAFLD), which can be treated or prevented by administration of an ApoCIII antagonist to increase LPL activity. Non-alcoholic fatty liver disease occurs when fat is deposited in the liver not due to excessive alcohol use. NAFLD is associated with insulin resistance and metabolic syndrome (obesity, combined hyperlipidemia, diabetes mellitus (type II) and high blood pressure. Patients with NAFLD usually have elevated liver enzymes and steatosis (e.g., as shown by a liver ultrasound). Extensive liver steatosis results NAFLD progressing into an advanced stage known as non-alcoholic steatohepatitis (NASH). NASH is a potentially life threatening condition with the only effective treatment a liver transplant. A liver biopsy can be used to assess the severity of the inflammation and resultant fibrosis, but is highly inaccurate with 75% of all cryptogenic liver transplants receiving a diagnosis of NASH post-transplant surgery. Thus, in some examples, the subject treated has NAFLD or NASH as diagnosed by imaging (e.g., MRI, CT, or ultrasound) or by biopsy, or other assay, such as a FibroTest. Thus the disclosed methods can reduce one or more of symptoms of NAFLD or NASH, such as elevated liver enzymes (such as one or more of albumin, alanine transaminase, aspartate transaminase, transaminitis, alkaline phosphatase, bilirubin, or gamma glutamyl transpeptidase) or steatosis, by at least 20%, at least 30%, at least 40%, at least 50%, at least 75%, or at least 90%, for example as compared to the absence of the ApoCIII antagonist. In some examples, the subject to be treated has a blood albumin level of at 6 g/dL, at least 10 g/dL, or at least 50 g/dL, a blood alanine transaminase (ALT) level of at least 70 IU/L, at least 100 IU/L, or at least 250 IU/L, a blood aspartate transaminase (AST) level of at least 50 IU/L, at least 100 IU/L, or at least 300 IU/L, a blood alkaline phosphatase (ALP) level of at least 150 IU/L, at least 200 IU/L, or at least 500 IU/L, a blood total bilirubin level of at least 2 mg/dL, at least 10 mg/dL, or at least 100 mg/dL, or combinations thereof. In some examples, the methods further include determining one or more blood liver enzyme levels and/or the level of liver steatosis in the subject, for example before and/or after administration of the ApoCIII antagonist.

In one example, the subject has or is at risk to develop type 2 diabetes mellitus, which can be treated or prevented (for example in predisposed subjects) by increased LPL activity. Type 2 diabetes mellitus is a metabolic disorder characterized by high blood glucose in the context of insulin resistance and relative insulin deficiency. Symptoms include excess thirst, frequent urination, and constant hunger. In one example, a subject with type 2 diabetes mellitus has one raised glucose reading with symptoms, or raised values on two occasions, of either: fasting plasma glucose ≥7.0 mmol/l (126 mg/dl) or with a glucose tolerance test, two hours after the oral dose a plasma glucose ≥11.1 mmol/l (200 mg/dl). A random blood sugar of greater than 11.1 mmol/l (200 mg/dL) in association with typical symptoms or a glycated hemoglobin (HbA1c) of greater than 6.5% is another method of diagnosing diabetes. Thus the disclosed methods can reduce one or more of these symptoms, such as reduce the blood glucose as detected by glucose tolerance test or fasting glucose by at least 10%, at least 20%, at least 40%, at least 50%, or at least 75%, for example as compared to the absence of the ApoCIII antagonist. In some examples, the methods further include determining a blood glucose level in the subject, for example before and/or after administration of the ApoCIII antagonist.

The following examples are provided to illustrate certain particular features and/or embodiments. These examples should not be construed to limit the disclosure to the particular features or embodiments described.

Example 1

Binding Specificity of ApoCIII mAb

This example describes methods used to demonstrate the binding specificity of the anti-human apolipoprotein CIII (ApoCIII) rabbit mAb from Epitomics.

The specificity and quality of the mAb (cat#2216-1, clone EP1372Y) was determined using mass spectrometry (MS) detection. The ability of the mAb to affinity retrieve ApoCIII from a number of different formats was determined. These forms included ApoCIII from plasma, as well as when bound to a VLDL particle in the form of VLDL standard (Academy Biomedical, Houston, Tex. catalog #33A-G2) or as a fluorescent VLDL probe (Kalen Biomedical, LLC, Montgomery Village, Md. catalog #770130-9). This reagent was also directly tested against cynomolgus monkey ApoCIII in the evaluation of cross-species interaction.

The characterization of the affinity reagents was performed using standard immuno-precipitation techniques, followed by top down MS detection. The resultant top-down mass spectra showed the ability the Ab reagents to bind to ApoCIII, in a variety of forms from each tested biological matrix.

As shown in FIG. 1, the mAb was able to repeatedly detect ApoCIII from 10 µL of human plasma diluted in PBS. This includes the different glycoform variants.

Figure 2:
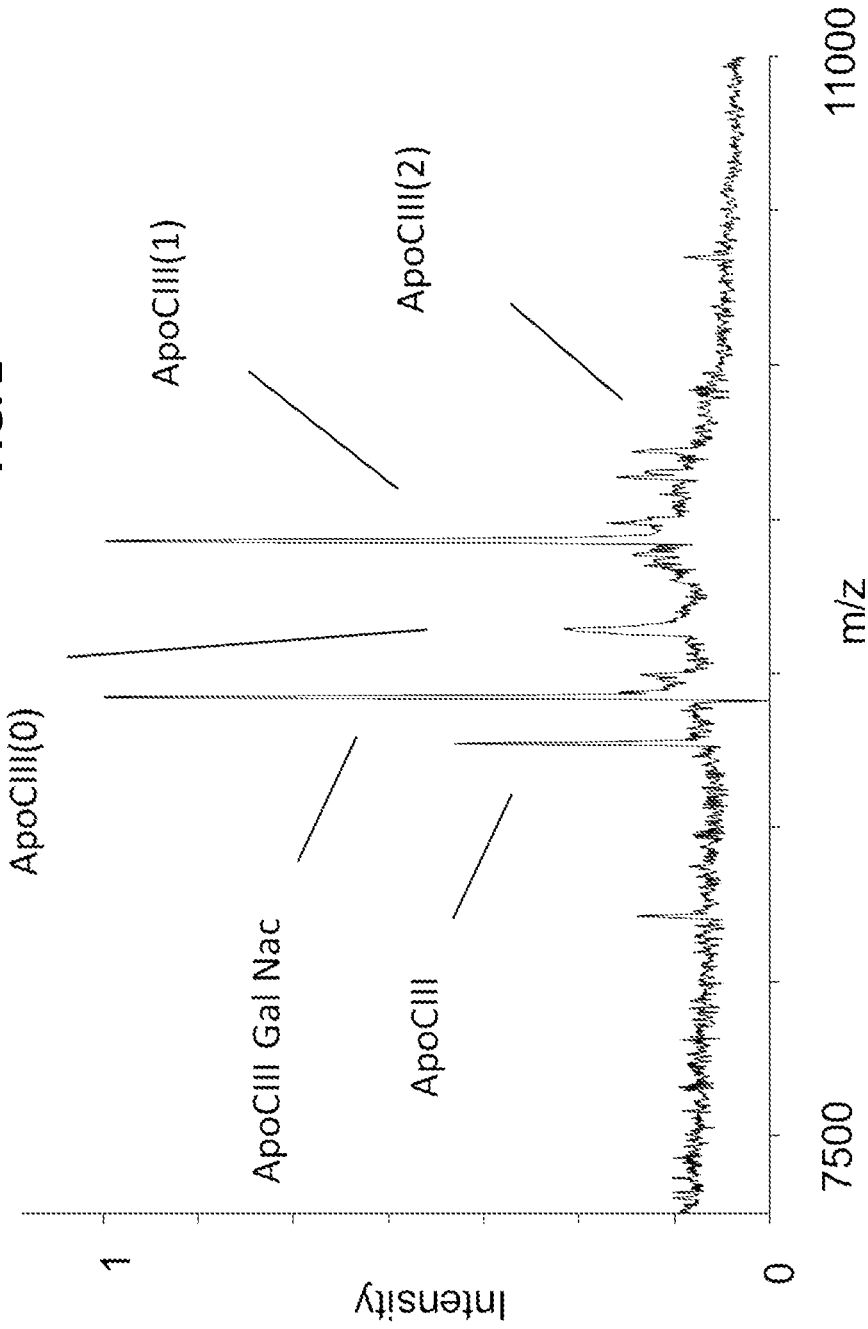
FIG. 2 is a graph showing a mass spectrometry trace and the ability of an ApoCIII mAb to detect ApoCIII that is bound to a VLDL standard.

As shown in FIG. 2, the mAb was able to detect ApoCIII from the VLDL standard reagent. The analysis of 20 µL of 0.6 mg/mL VLDL standard was able to render a mass spectral profile that also includes the different glycoforms present. This establishes the ability of the mAb to bind to ApoCIII imbedded in the VLDL, and demonstrates that the VLDL standard contains ApoCIII that resembles what is present in a plasma sample.

Figure 3:
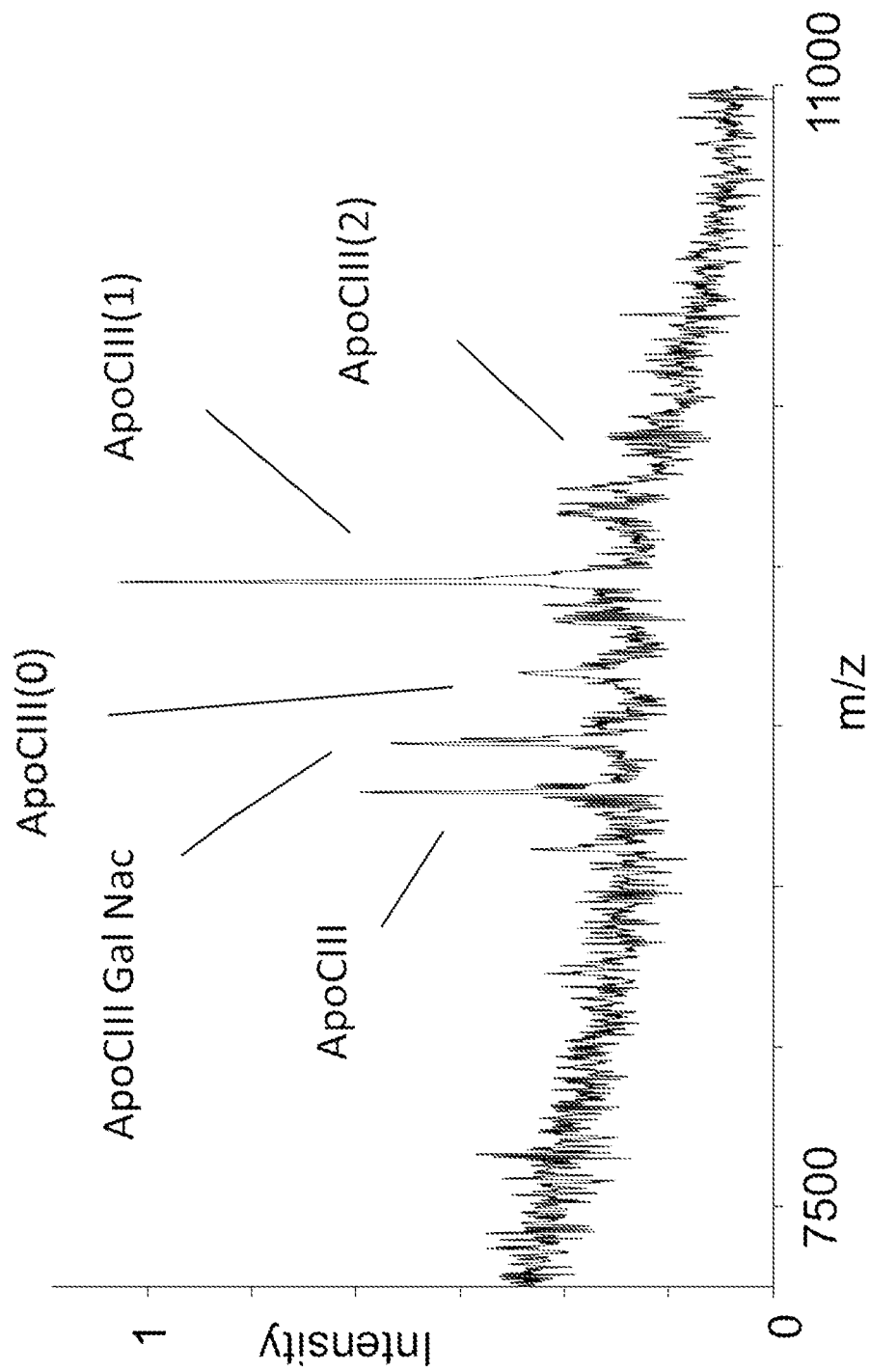
FIG. 3 is a graph showing a mass spectrometry trace and the ability of an ApoCIII mAb to detect ApoCIII incorporated into a human VLDL probe.

As shown in FIG. 3, the mAb was able to detect a probe that was comprised of DiL-labeled VLDL particles, which are initially highly fluorescent but decrease in intensity as the lipid particle is digested and the DiL comes in contact with the aqueous environment. The IP was performed using 5 µL of the 0.5 mg/mL probe sample that was diluted in PBS. The mAb was able to retrieve the different variants of ApoCIII present in the VLDL probe. As with the non-labeled VLDL standard, these results simultaneously demonstrate the mAb's ability to bind the VLDL embedded ApoCIII, and that the VLDL probe reagent used contains ApoCIII.

Figure 4:
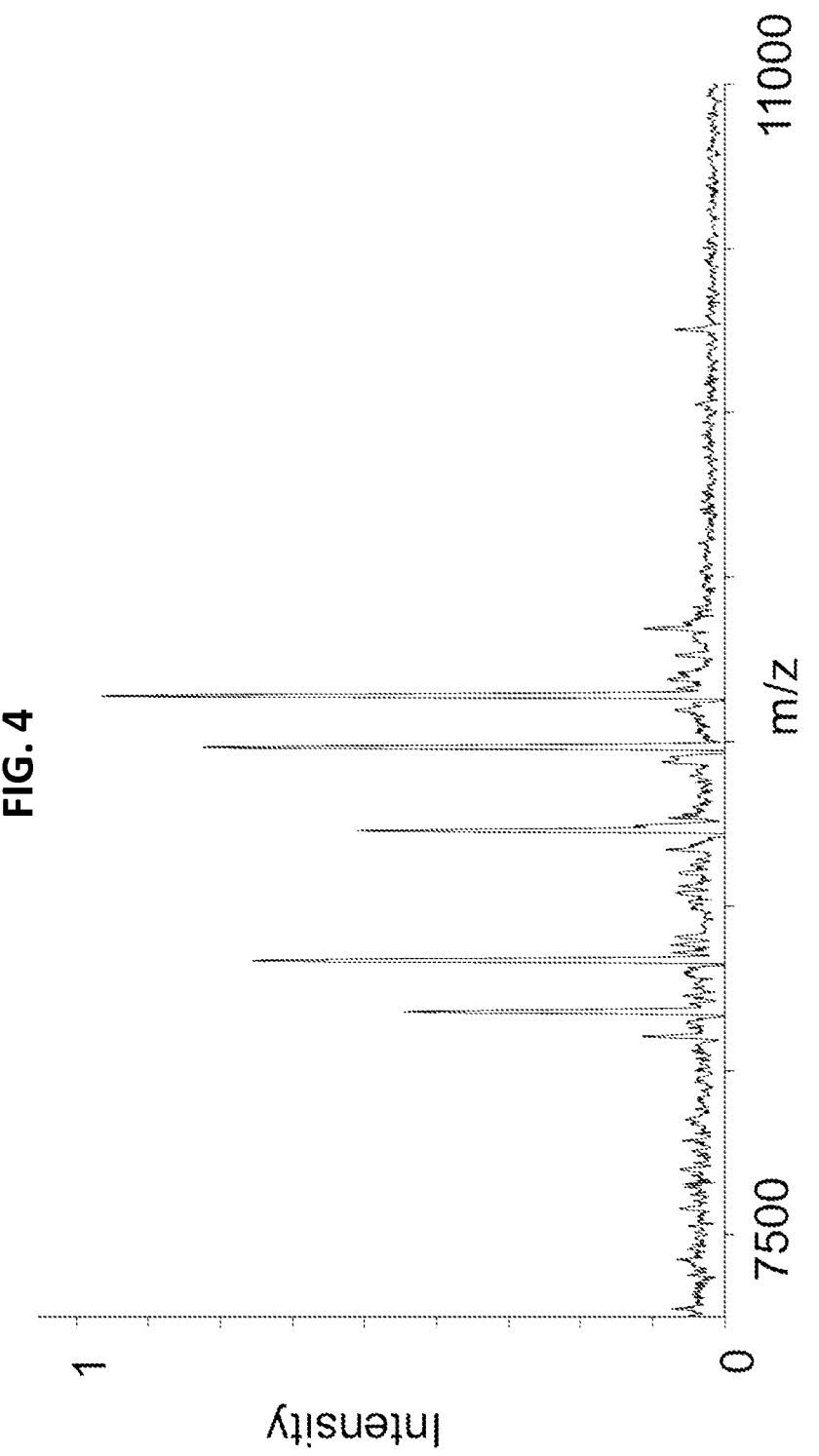
FIG. 4 is a graph showing a mass spectrometry trace and the ability of an ApoCIII mAb to detect free ApoCIII in cynomologus monkey plasma. As cynomolgus monkey ApoCIII has not been fully characterized previously, it is difficult to assign identifications to the observed MS peaks. Their origin has been confirmed with two anti-ApoCIII antibodies and against non-ApoCIII antibodies (negative controls) for non-specific binding. However, it is known that the ApoCIII C-terminus is highly conserved between human and this non-human protein (NHP), with both having the threonine in the same position for the o-linked glycosylation. This region of human and non-human primate ApoCIII is not congruent with the known molecular biology found in rodents.

As shown in FIG. 4, the mAb was able to detect ApoCIII in cynomologus monkey plasma (non-human protein). These experiments used 10 µL of plasma.

To estimate the amount of ApoCIII present with both the VLDL Probe and the Human VLDL Standard, the following methods were used. The concentration of ApoCIII in the VLDL Probe and Standard were determined using routine MS quantitative techniques following the immuno-precipitation method applied above. This approach was based off of signal integral readings normalized to an exogenous reference standard. These values were determined to be 23.88 and 20.83 ug/mL, respectively.

In summary, the MS results show that the Epitomics ApoCIII mAb can bind to human and cynomologus monkey ApoCIII, ApoCIII can still be recognized by the mAb while bound to VLDL particles, and confirmed the presence of ApoCIII in these commercially available reagents. Since the mAb used specifically targets the C-terminus of the ApoCIII molecule, these results indicate that this end of ApoCIII is at least partially exposed while it is associated in the VLDL particle. Also, the binding of the cynomologus monkey ApoCIII to the mAb supports the use of the same Ab DNA for the generation of a chimeric in animal model testing.

Example 2

This example describes methods used to demonstrate that the anti-human ApoCIII mAb from Epitopmics (see Example 1) can preserve the biological activity of LPL by retarding the inhibitory effects of ApoCIII.

For these experiments, LPL was from post-heparinized heparin plasma collected from three male volunteers after a >8 hour fast. The collected samples were processed and stored at −80° C. until ready for use. The test system is a fluorescence assay that utilizes the same VLDL Probe that was analyzed and described in Example 1. To reiterate, the VLDL Probe is a purified VLDL standard labeled with DiL, a tracer that is highly fluorescent when embedded within the fatty acids chains present in the intact VLDL particle. However, when the DiL becomes exposed to an aqueous environment, as when the probe is digested by LPL, the fluorescence is lost. VLDL is the specific substrate of LPL and this system was determined to be the best in eliminating interference from other lipases that are present the LPL source. It is also widely understood that in the LPL conversion of VLDL to LDL, all ApoCIII is removed from the lipoprotein particle, and released into the blood stream. For this functional determination, a series of controls were run to establish confidence in this prototype functional bioassay.

Figure 5:
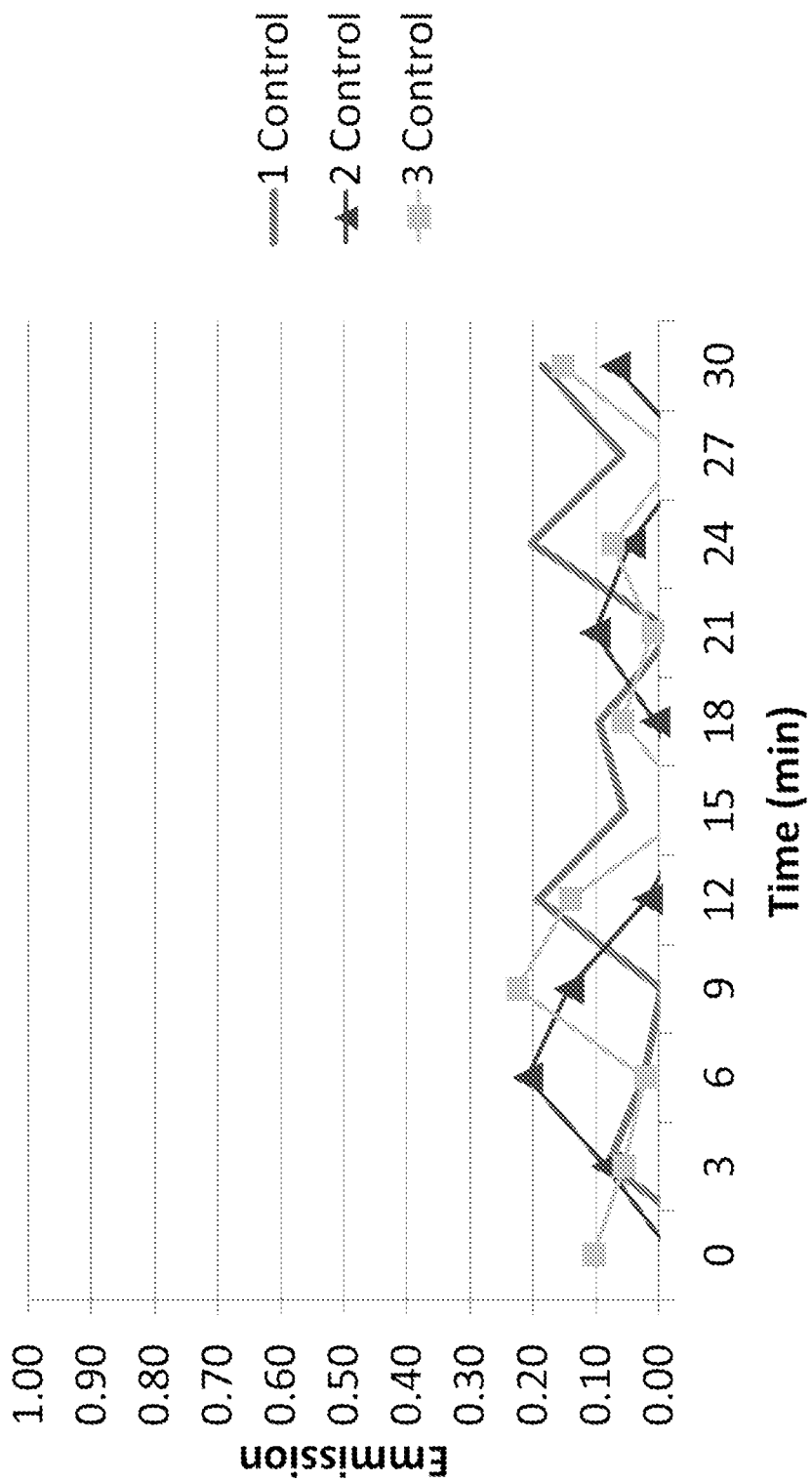
FIG. 5 is a graph showing the baseline fluorescence for three fasting post heparinized heparin human plasma samples. The plot shows that the background fluorescence observed within these samples is nominal.

The baseline fluorescence for each of the three plasma samples was established as shown in FIG. 5, which shows that the background fluorescence observed within these samples is nominal. The samples run were 50 µL of plasma (the LPL source) in 100 µL of TRIS at pH 8.5 with 10 g/L BSA. The reaction was run for a total of 30 minutes with readings (488-565 nm) occurring every 3 minutes.

Figure 6:
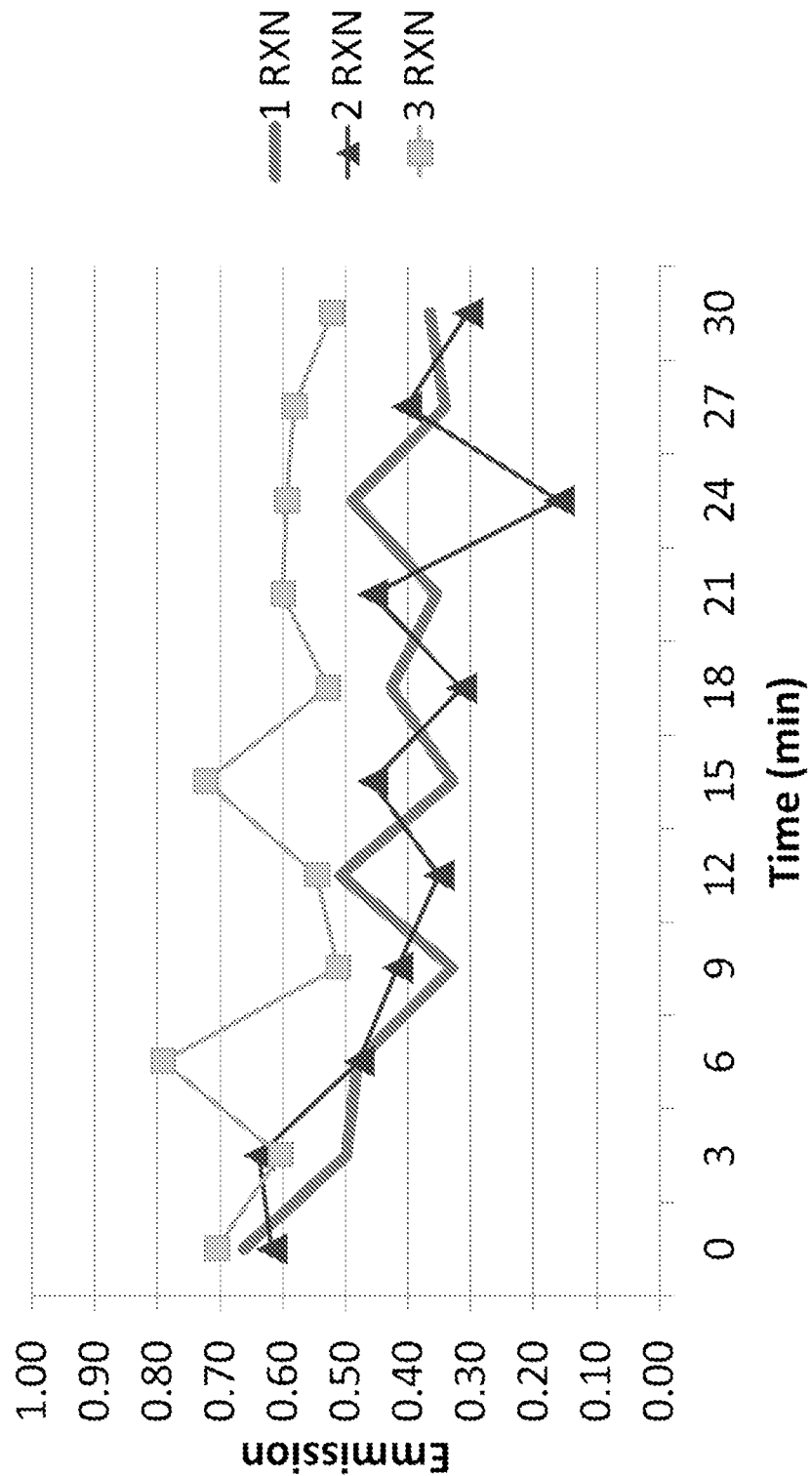
FIG. 6 is a graph showing digestion of the fluorescent VLDL probe (MS trace shown in FIG. 3) by endogenous LPL present in each of the plasma samples (as evidenced by a decrease in fluorescent signal).

To test the VLDL Probe reaction with the LPL present within each of the three plasma sources, 40 µL of a 1:10 dilution of the VLDL Probe (Kalen Biomedical, LLC, Montgomery Village, Md.) was mixed with each sample. The Probe was diluted in the sample diluent and the test volume remained at 150 µL. The reaction proceeded for 30 minutes, in the same fashion as the plasma controls. As shown in FIG. 6 the Probe behaved as expected, with an observable decrease in signal over the course of the run, as a result of LPL in the plasma digesting the VLDL Probe. The decrease in the fluorescence emission ranged from ~21-50% between the three samples. The VLDL Probe included ApoCIII, ~1.02 pmoles, but the substrate conversion still proceeded over the time course monitored.

Figure 7:
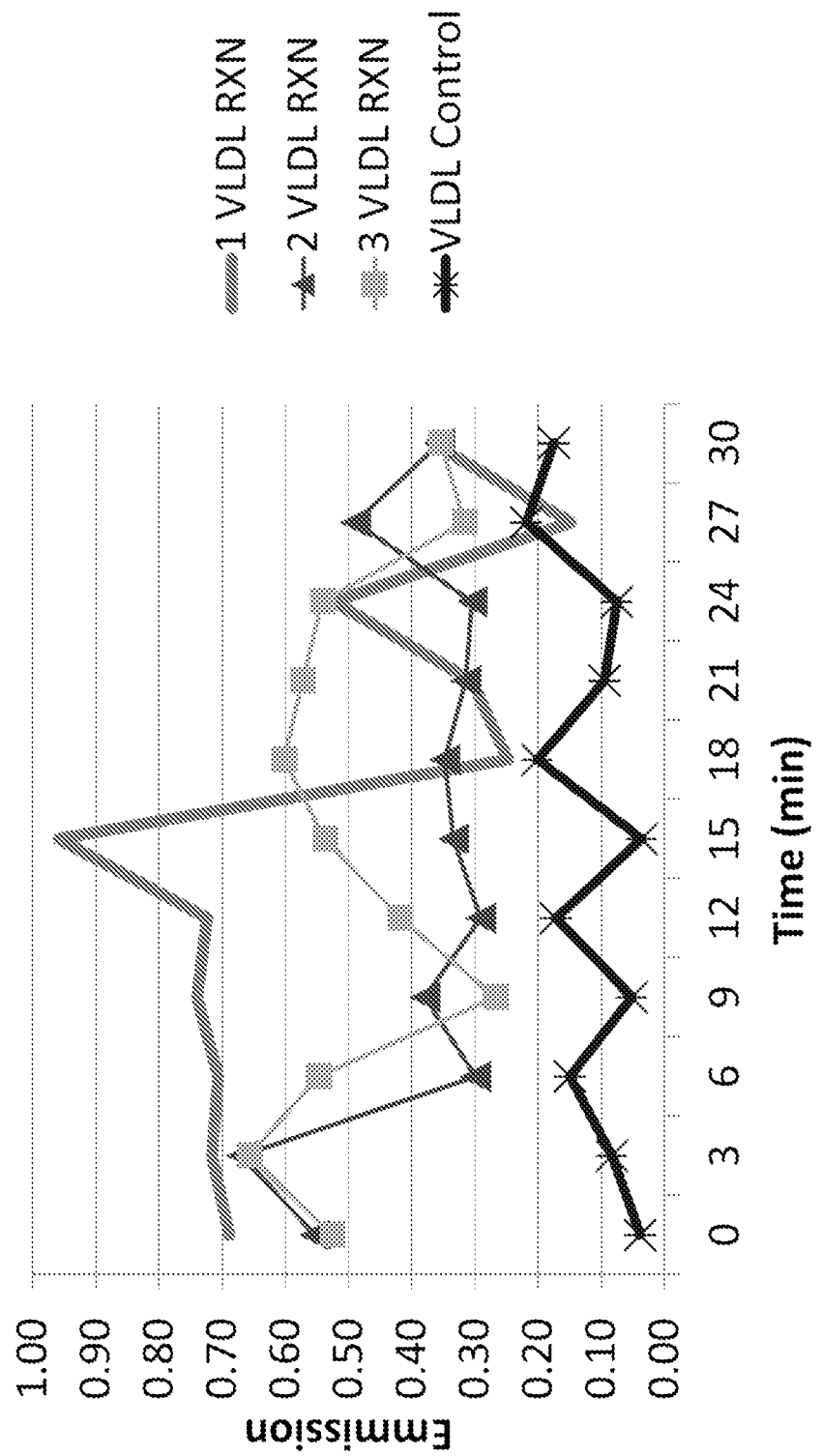
FIG. 7 is a graph showing digestion of the VLDL probe by endogenous LPL in each of the three plasma samples (as evidenced by a decrease in fluorescent signal). However, the sample differs from those shown in FIG. 6 as they were enriched with ApoCIII via the addition of a VLDL standard (MS trace shown in FIG. 2).

The effect of an increase in ApoCIII in the system, in either the form of VLDL bound or as free ApoCIII, was determined. The same sample setup as above was used, including the VLDL probe, except that an approximately equal amount of ApoCIII was added as either VLDL Standard or free. In either case, the system now had approximately double the amount of exogenous ApoCIII as with the Probe alone, at a total addition of 2 pmoles. FIG. 7 shows the response to the addition of VLDL bound ApoCIII. The observed responses show that the LPL conversion of the Probe still occurred, and the approximate change over the course of the reaction ranged from 33-50%. This conversion rate is very similar to what was observed in the control reactions. A possible explanation for the choppiness is the introduction of glycerol into the system as the Probe and the VLDL Standard come from the manufacturer containing 50% glycerol.

Figure 8:
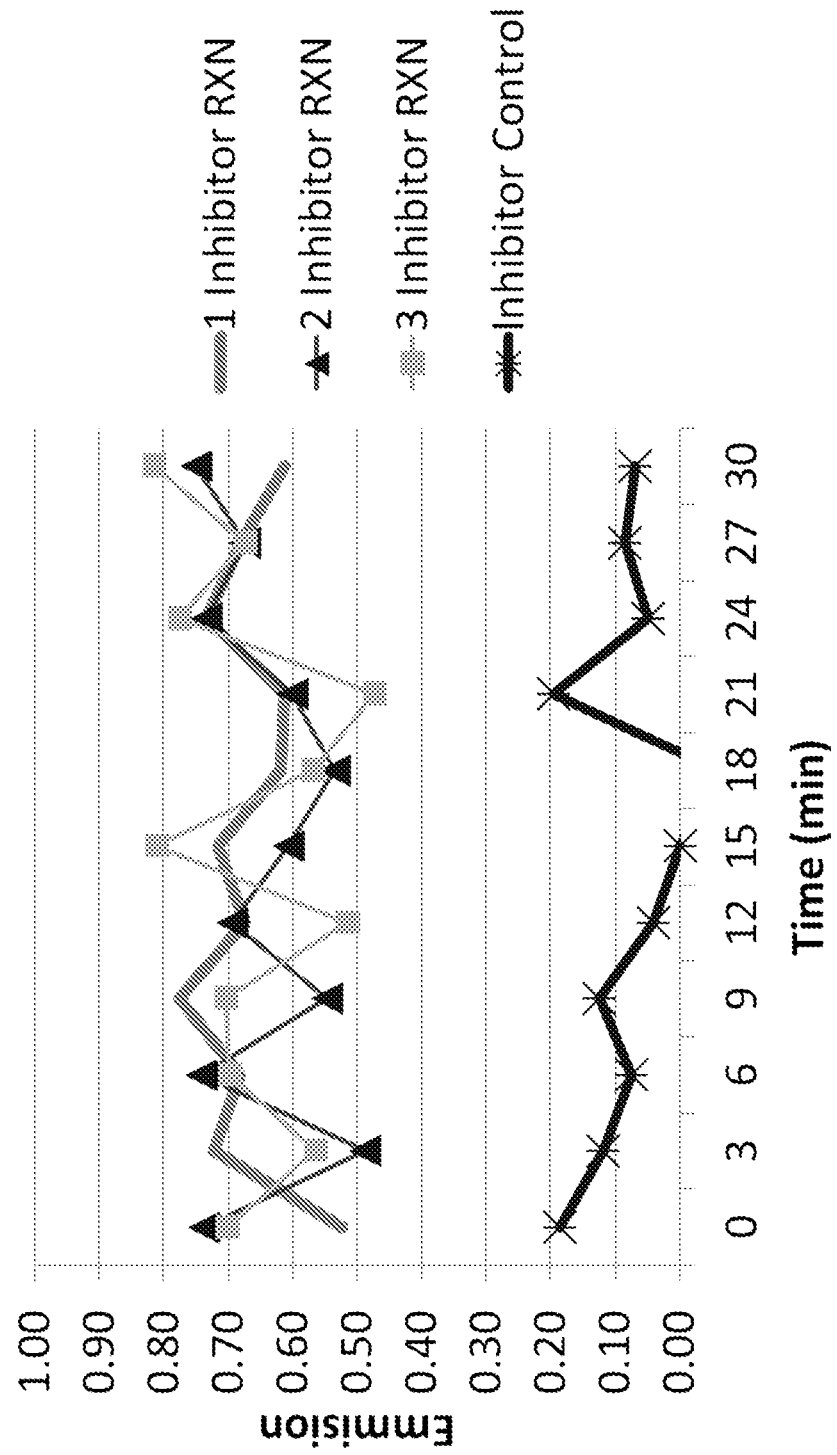
FIG. 8 is a graph showing that the addition of free ApoCIII results in the complete shutdown of LPL activity in all three human samples (as evidenced by the lack of change in the probe signal). The amount of free ApoCIII added to the reaction was equal to the amount of ApoCIII bound within the VLDL standard.

FIG. 8 shows the results of the same experiment, but with the introduction of free ApoCIII into the system, not VLDL bound. As with FIG. 7, the total amount of exogenous ApoCIII in the system was ~2 picomoles, but ~1.1 picomoles was from the free ApoCIII.

As shown in FIG. 8, the addition of free ApoCIII resulted in the complete shutdown of LPL in all three samples. These results, in combination with the VLDL bound ApoCIII (FIG. 7), were not expected and indicate that free ApoCIII, not bound to VLDL, is truly culprit when examining LPL activity. When VLDL is digested by LPL, the particle is stripped of all ApoCIII by the time it is transformed into LDL. During this process, the liberated ApoCIII is released into the blood stream. The fate of the free ApoCIII, as understood by those in the art, is that it is scavenged by either other VLDL particles or HDL particles. If incorporated into another VLDL, it will continue in this cycle. On the other hand, ApoCIII incorporated into HDL results in either hepatic uptake or renal clearance. Either of the latter results in removal from the system. When considering this as a whole biological system, and the prevalence of simple feed-back mechanisms present within the body, it appears that the body uses free ApoCIII to control the rate of lipid metabolism. In this case, preventing the binding of free ApoCIII to the LPL can be used to increase or restore LPL activity.

Figure 9:
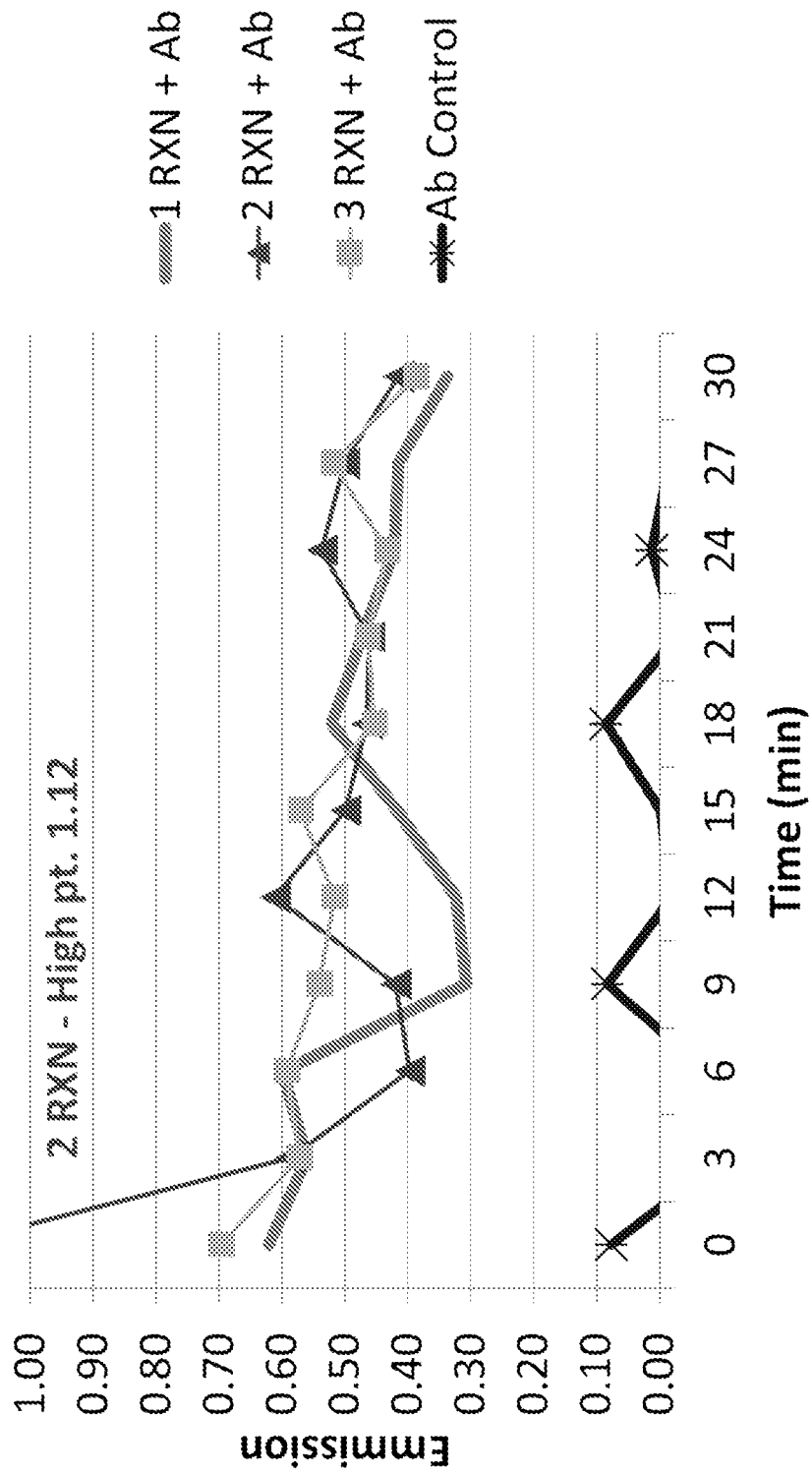
FIG. 9 is a graph showing digestion of the VLDL probe by the endogenous LPL in the three different human plasmas, but in the presence of an ApoCIII mAb (as evidenced by a decrease in fluorescent signal).

To evaluate the effect of the ApoCIII mAb on this in vitro system, the mAb was added to the system described above just prior to the addition of the Probe. FIG. 9 shows a repeat of the general Probe VLDL reaction with the addition of 333 femtomoles of ApoCIII mAb. This amount of mAb would translate into a 5 mg dose of a therapeutic (for example in a human). As shown in FIG. 9, addition of the mAb to the reaction system did not alter the results. The observed conversion range was ~41-60%. This is a bit better than the original run (FIG. 6), and may be attributable to the mAb binding to ApoCIII that is liberated either from the probe or from an endogenous VLDL source. Thus, it appears that it is not until the ApoCIII becomes liberated ("free" ApoCIII) from the VLDL that it has an inhibitory effect. If this experiment were conduced for an extended incubation period, it is likely progressively more inhibition would be observed in samples with higher concentrations of VLDL than lower concentrations.

Figure 10:
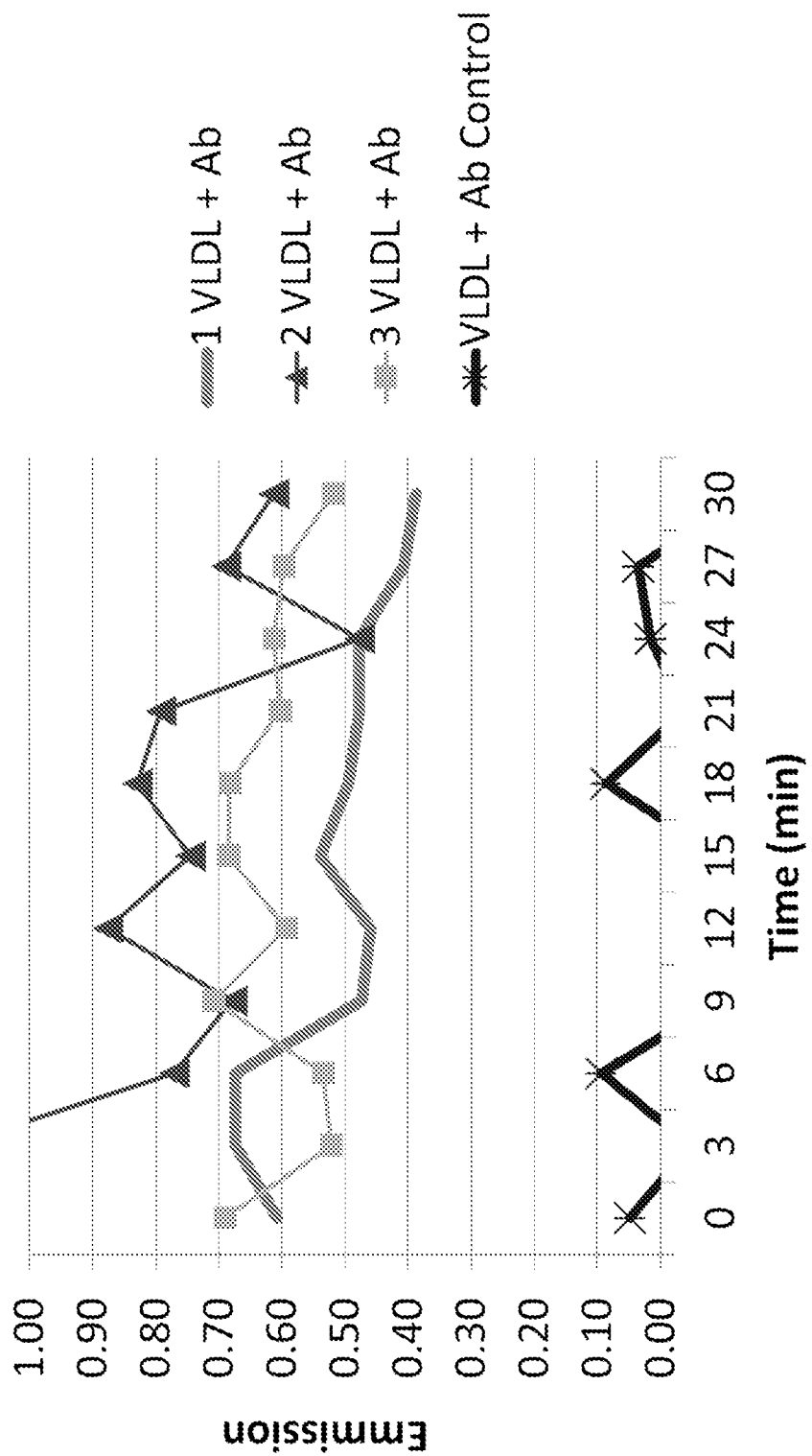
FIG. 10 is a graph showing digestion of the VLDL probe by LPL found in the human plasma samples, but in the presence of an ApoCIII mAb and with an increase in ApoCIII concentration by addition of the VLDL standard (containing bound ApoCIII).

The effect of the ApoCIII mAb on the presence of increasing concentrations of ApoCIII, introduced through the addition of either VLDL standard (with bound ApoCIII) or free ApoCIII, was determined. The same protocol as above was used, but with the addition of 333 femtomoles of the mAb. As shown in FIG. 10, LPL function was maintained. This was expected as the addition of the VLDL standard did not retard the reaction (FIG. 9). As shown in FIG. 10, the decrease of the fluorescence emission continued over the course of the 30 minute reaction. The observed decrease in emission ranged from 29-47%.

Figure 11:
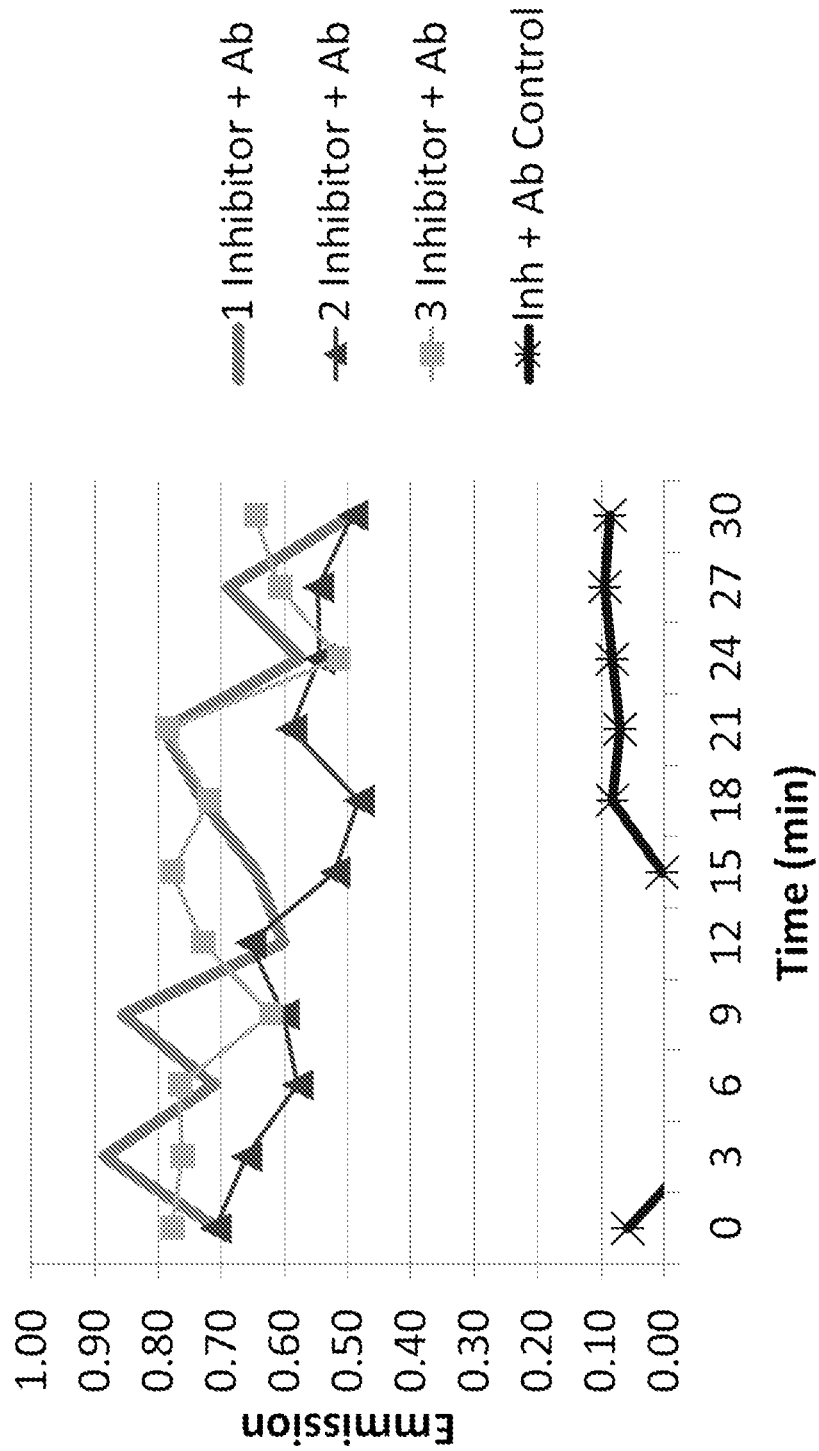
FIG. 11 is a graph showing digestion of the VLDL probe by the LPL in the three different plasma samples, but in the presence of an ApoCIII mAb and free ApoCIII. Probe digestion occurred as evident in the decrease of observed fluorescent signal.

FIG. 11 shows the results from the addition of the mAb when the system was spiked with free ApoCIII. As with the previous experiments, the fundamental parameters were kept the same and 333 femtomoles mAb was added just prior to the addition of the Probe. The reaction proceeded for 30 minutes with the net result demonstrating the preservation of LPL activity. The conversion observed was 18-29%. Even though the observed reaction rate is less than with previous conditions, LPL function was still present, unlike that observed in the treatment of the system with free ApoCIII that had previously shutoff all LPL activity (see FIG. 8). Since the ApoCIII (2 pmoles) is being added in excess over the inhibitor (333 femtomoles), the benefit observed is significant.

In summary, the results provided herein confirm that the binding of ApoCIII inhibits the function of LPL at the molecular level, and that this inhibition can be reversed by use of an ApoCIII antagonist.

Example 3

ApoCIII Antibodies

This example describes methods that can be used to make other antibodies to the C-terminal region of ApoCIII (e.g., SEQ ID NO: 1 or at least 5, at least 6, at least 7, at least 8, at least 9 or at least 10 contiguous amino acids of SEQ ID NO: 1), which antagonize the activity of ApoCIII.

Methods of making antibodies are routine in the art. For example, monoclonal antibodies to the C-terminal region of ApoCIII can be prepared from murine hybridomas according to the classic method of Kohler & Milstein (*Nature* 256:495, 1975) or a derivative method thereof. Polyclonal antiserum containing antibodies to the heterogeneous epitopes of the C-terminal region of ApoCIII can be prepared by immunizing suitable animals with the peptide, which can be unmodified or modified to enhance immunogenicity. An effective immunization protocol for rabbits can be found in Vaitukaitis et al. (*J. Clin. Endocrinol. Metab.* 33:988-91, 1971).

For example, a peptide comprising at least 6 contiguous amino acids from the C-terminal region of ApoCIII (such as 6, 7, 8, 9, or 10 contiguous amino acids from the C-terminal 39, C-terminal 30, or C-terminal 20 amino acids of ApoCIII) can be injected into an animal (e.g., mouse, rabbit) for the production of antibodies to that peptide. In some examples the ApoCIII peptide is conjugated to another molecule to increase its antigenicity. The ability of the antibody to specifically bind ApoCIII can be determined using routine methods, such as Western blotting, immunohistochemistry, or MS (see Example 1). The ability of the antibody to inhibit ApoCIII activity, and increase LPL activity, can be determined using a fluorescently labeled VLDL probe (see Example 1).

The resulting antibodies have ApoCIII antagonistic activity can be used to generate a humanized or fully human mAb, and can be used to generate a fragment Ab (FAb). These procedures are now considered routine in application and are readily performed.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A method of increasing the activity of lipoprotein lipase (LPL), comprising:
   contacting apolipoprotein C III (ApoCIII) with an effective amount of an agent, wherein the agent consists of a monoclonal antibody or an antibody fragment thereof that binds to the C-terminus of ApoCIII and antagonizes the inhibitory action of free ApoCIII, thereby increasing LPL activity.

2. The method of claim 1, wherein the method is performed in vitro.

3. The method of claim 1, wherein the monoclonal antibody or antibody fragment thereof that antagonizes the inhibitory action of free ApoCIII is rabbit mAb Epitomics catalog number 2216-1.

4. The method of claim 1, wherein the monoclonal antibody or antibody fragment thereof binds to amino acids 41-79 of SEQ ID NO:1.

* * * * *

SEQUENCE LISTING

<160> NUMBER OF SEQ ID NOS: 1

<210> SEQ ID NO 1
<211> LENGTH: 39
<212> TYPE: PRT
<213> ORGANISM: Homo sapiens

<400> SEQUENCE: 1

Gly Trp Val Thr Asp Gly Phe Ser Ser Leu Lys Asp Tyr Trp Ser Thr
1               5                   10                  15

Val Lys Asp Lys Phe Ser Glu Phe Trp Asp Leu Asp Pro Glu Val Arg
            20                  25                  30

Pro Thr Ser Ala Val Ala Ala
        35